(12) United States Patent
Edelbrock (10) Patent No.: US 7,939,019 B2
(45) Date of Patent: May 10, 2011

(54) SENSOR PACKAGE WITH AN INTERIM AUTO-CALIBRATION CIRCUIT

(75) Inventor: Andrew J. Edelbrock, Granger, IN (US)

(73) Assignee: Bayer HealthCare LLC, Tarrytown, NY (US)

( * ) Notice: Subject to any disclaimer, the term of this patent is extended or adjusted under 35 U.S.C. 154(b) by 632 days.

(21) Appl. No.: 11/920,301

(22) PCT Filed: May 22, 2006

(86) PCT No.: PCT/US2006/019796
§ 371 (c)(1),
(2), (4) Date: Nov. 13, 2007

(87) PCT Pub. No.: WO2006/127635
PCT Pub. Date: Nov. 30, 2006

(65) Prior Publication Data
US 2009/0087347 A1    Apr. 2, 2009

Related U.S. Application Data

(60) Provisional application No. 60/683,885, filed on May 24, 2005.

(51) Int. Cl.
*G01N 21/00* (2006.01)
(52) U.S. Cl. ............... 422/64; 422/62; 422/63; 422/65; 422/99; 422/100; 436/180
(58) Field of Classification Search ............... 422/68.1, 422/99–100, 62–65; 436/180
See application file for complete search history.

(56) References Cited

U.S. PATENT DOCUMENTS

| 5,366,609 A | 11/1994 | White et al. ............ 204/403 |
| 5,575,403 A | 11/1996 | Charlton et al. ............ 221/31 |
| 5,597,532 A | 1/1997 | Connolly .................. 422/58 |
| 5,628,890 A | 5/1997 | Carter et al. ............ 204/403 |
| 5,630,986 A | 5/1997 | Charlton et al. ............ 422/64 |
| 5,700,695 A | 12/1997 | Yassinzadeh et al. ...... 436/180 |

(Continued)

FOREIGN PATENT DOCUMENTS
EP    1 174 716 A2    7/2001
(Continued)

OTHER PUBLICATIONS

Written Opinion corresponding to International Patent Application No. PCT/US2006/019796, European Patent Office, dated Oct. 13, 2006, 5 pages.

(Continued)

*Primary Examiner* — Jyoti Nagpaul
(74) *Attorney, Agent, or Firm* — Nixon Peabody LLP (57) ABSTRACT

An interim auto-calibration circuit or label adapted to be used with a sensor package. The sensor package is adapted to be used with first and second instruments to determine the analyte concentration of fluid sample. The instruments are different and include respective first and second plurality of pins that are in different patterns. The sensor package comprises a plurality of electrical connections that includes a plurality of contact areas. The contact areas have a first and second contact sections being shorted together. The first contact sections are adapted to contact a respective one of the first pins. The second contact sections are adapted to contact a respective one of the second pins. The electrical connections assist in conveying information corresponding to the test sensors. The information is adapted to be utilized by the first and the second instruments to auto-calibrate for the test sensors.

16 Claims, 4 Drawing Sheets

U.S. PATENT DOCUMENTS

| | | | |
|---|---|---|---|
| 5,856,195 A | 1/1999 | Charlton et al. | 436/50 |
| 6,102,872 A | 8/2000 | Doneen et al. | 600/582 |
| 6,531,040 B2 | 3/2003 | Musho et al. | 204/401 |

FOREIGN PATENT DOCUMENTS

| | | | |
|---|---|---|---|
| EP | 1 288 653 A1 | 3/2003 |
| EP | 1 398 631 A2 | 3/2004 |
| EP | 1 431 758 A1 | 6/2004 |
| EP | 0 840 122 B1 | 9/2004 |
| WO | WO 2004/113911 A1 | 12/2004 |
| WO | WO 2004/113915 A1 | 12/2004 |

OTHER PUBLICATIONS

International Search Report corresponding to International Patent Application No. PCT/US2006/019796, European Patent Office, dated Oct. 13, 2006, 3 pages.

SENSOR PACKAGE WITH AN INTERIM AUTO-CALIBRATION CIRCUIT

CROSS-REFERENCE TO RELATED APPLICATIONS

This application claims priority to Application No. 60/683,885 filed on May 24, 2005, which is incorporated by reference in its entirety.

FIELD OF THE INVENTION

The present invention generally relates to a sensor package with an interim auto-calibration circuit or label and methods of forming the same. The interim auto-calibration circuits or labels are adapted to be used in calibrating instruments or meters that determine the concentration of an analyte (e.g., glucose) in a fluid.

BACKGROUND OF THE INVENTION

The quantitative determination of analytes in body fluids is of great importance in the diagnoses and maintenance of certain physiological abnormalities. For example, lactate, cholesterol and bilirubin should be monitored in certain individuals. In particular, it is important to diabetic individuals to frequently check the glucose level in their body fluids to regulate the glucose intake in their diets. The results of such tests can be used to determine what, if any, insulin or other medication needs to be administered. In one type of blood-glucose testing system, sensors are used to test a sample of blood.

A test sensor contains biosensing or reagent material that reacts with blood glucose. The testing end of the sensor is adapted to be placed into the fluid being tested, for example, blood that has accumulated on a person's finger after the finger has been pricked. The fluid is drawn into a capillary channel that extends in the sensor from the testing end to the reagent material by capillary action so that a sufficient amount of fluid to be tested is drawn into the sensor. The fluid then chemically reacts with the reagent material in the sensor resulting in an electrical signal indicative of the glucose level in the fluid being tested. This signal is supplied to the meter via contact areas located near the rear or contact end of the sensor and becomes the measured output.

A problem occurs when the test sensor is to be modified such as, for example, a modification in the reagent material. During the time period before the modified test sensor is to be launched, there exists significant inventory of existing test sensors. In the past, the manufacturer may have delayed launching the new modified test sensor until the existing test sensors were purged from the marketplace. One disadvantage of such a process is that the new system using the new modified test sensor cannot be realistically marketed until after it is in place. Another option for the manufacturer would be to swap the existing test sensors after the launch of the modified test sensor. This has the disadvantage of being costly since there are costs associated with removing existing product from the marketplace as well as opportunities lost if the existing test sensors cannot be used.

It would be desirable to provide a test sensor that would avoid the need to delay launch of a modified test sensor without the need to swap out the existing test sensor with the modified test sensor.

SUMMARY OF THE INVENTION

According to one embodiment, an interim auto-calibration circuit or label is adapted to be used with a sensor package. The sensor package is adapted to be used with a first instrument and a second instrument. The first instrument is adapted to determine an analyte concentration in a fluid sample. The second instrument is adapted to determine the analyte concentration in the fluid sample. The first instrument is different from the second instrument. The first instrument includes a first plurality of pins in a first pattern. The second instrument includes a second plurality of pins in a second pattern. The first and second patterns are different. The sensor package comprises a plurality of electrical connections that includes a plurality of contact areas. Each of the plurality of contact areas has a first contact section and a second contact section being shorted together. Each of the first contact sections is adapted to contact a respective one of the first plurality of pins. Each of the second contact sections is adapted to contact a respective one of the second plurality of pins. The plurality of electrical connections assists in conveying information corresponding to the plurality of test sensors. The information is adapted to be utilized by the first instrument and the second instrument to auto-calibrate for the plurality of test sensors.

According to another embodiment, a sensor package is adapted to be used in a first instrument and a second instrument. The first instrument is adapted to determine an analyte concentration in a fluid sample. The second instrument is adapted to determine the analyte concentration in the fluid sample. The first instrument is different from the second instrument. The first instrument includes a first plurality of pins in a first pattern. The second instrument includes a second plurality of pins in a second pattern. The first and second patterns are different. The sensor package comprises a plurality of test sensors and an interim auto-calibration circuit or label. The plurality of test sensors is adapted to receive the fluid sample and is operable with the first instrument and the second instrument. The interim auto-calibration circuit or label is adapted to be used with the first instrument and the second instrument. The auto-calibration circuit or label includes a plurality of electrical connections. The plurality of electrical connections includes a plurality of contact areas. Each of the plurality of contact areas has a first contact section and a second contact section being shorted together. Each of the first contact sections is adapted to contact a respective one of the first plurality of pins. Each of the second contact sections is adapted to contact a respective one of the second plurality of pins. The plurality of electrical connections assists in conveying information corresponding to the plurality of test sensors. The information is adapted to be utilized by the first instrument and the second instrument to auto-calibrate for the plurality of test sensors.

According to one embodiment, a system for determining an analyte concentration in a fluid sample comprises a test sensor, a processor and an interim auto-calibration circuit or label. The test sensor is adapted to receive the fluid sample. The processor is responsive to the test sensor and adapted to perform a predefined test sequence for measuring a predefined parameter value. The interim auto-calibration circuit or label is adapted to be used with the first instrument and the second instrument. The auto-calibration circuit or label includes a plurality of electrical connections. The plurality of electrical connections includes a plurality of contact areas. Each of the plurality of contact areas has a first contact section and a second contact section being shorted together. Each of the first contact sections is adapted to contact a respective one of the first plurality of pins. Each of the second contact sections is adapted to contact a respective one of the second plurality of pins. The plurality of electrical connections assists in conveying information corresponding to the plurality of test sensors. The information is adapted to be utilized by the first instrument and the second instrument to auto-calibrate for the plurality of test sensors.

DETAILED DESCRIPTION OF ILLUSTRATED EMBODIMENTS

An instrument or meter in one embodiment uses a test sensor adapted to receive a fluid sample to be analyzed, and a processor adapted to perform a predefined test sequence for measuring a predefined parameter value. A memory is coupled to the processor for storing predefined parameter data values. Calibration information associated with the test sensor may be read by the processor before the fluid sample to be measured is received. Calibration information may be read by the processor after the fluid sample to be measured is received, but not after the concentration of the analyte has been determined. Calibration information is used in measuring the predefined parameter data value to compensate for different characteristics of test sensors, which will vary on a batch-to-batch basis. Variations of this process will be apparent to those of ordinary skill in the art from the teachings disclosed herein, including but not limited to, the drawings.

Figure 1:
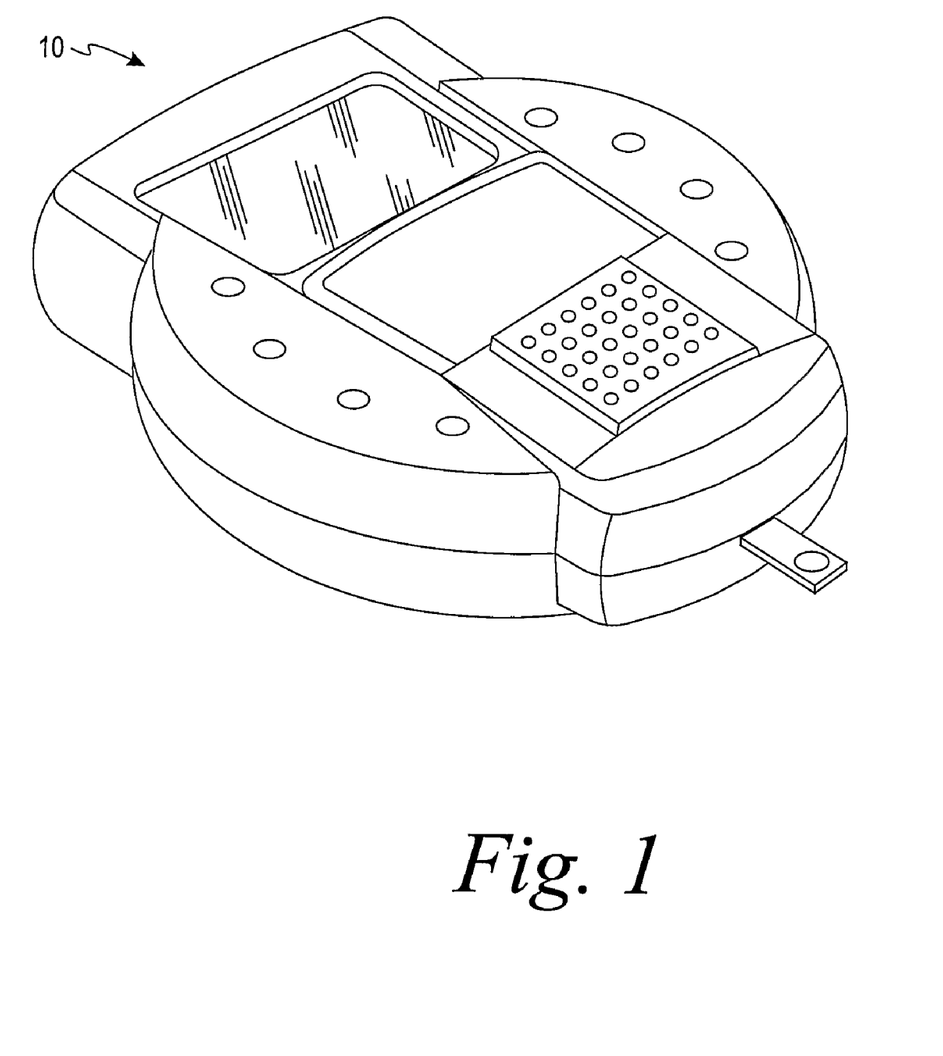
FIG. 1 is a sensing instrument according to one embodiment.
Figure 2:
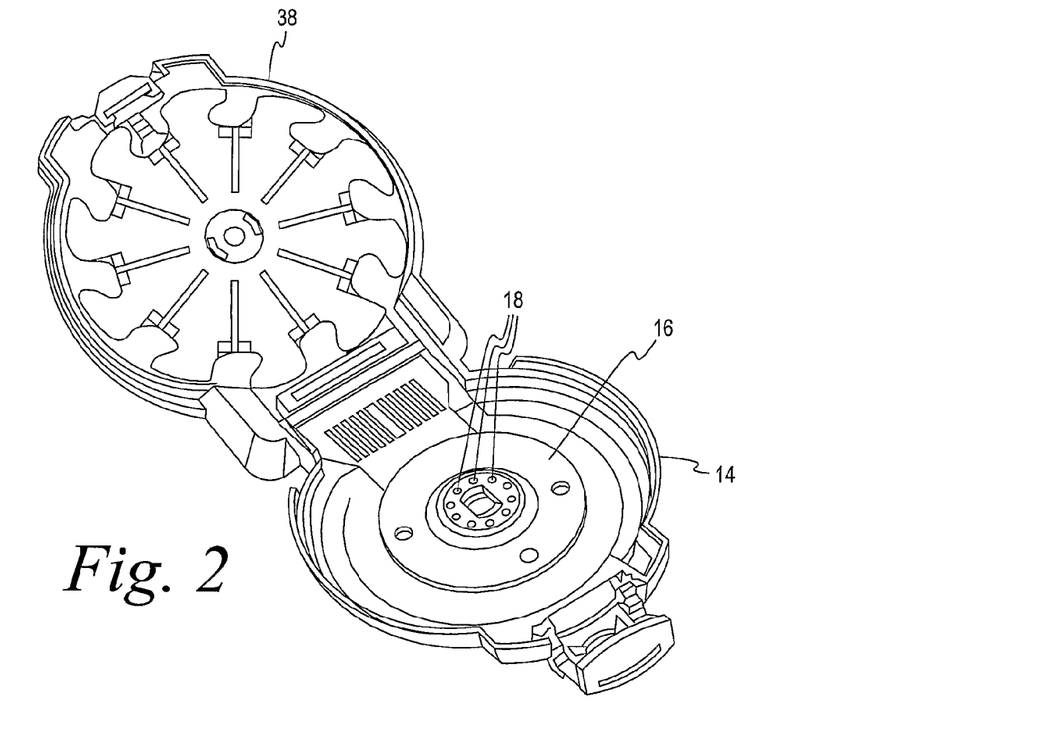
FIG. 2 is the interior of the sensing instrument of FIG. 1.
Figure 3:
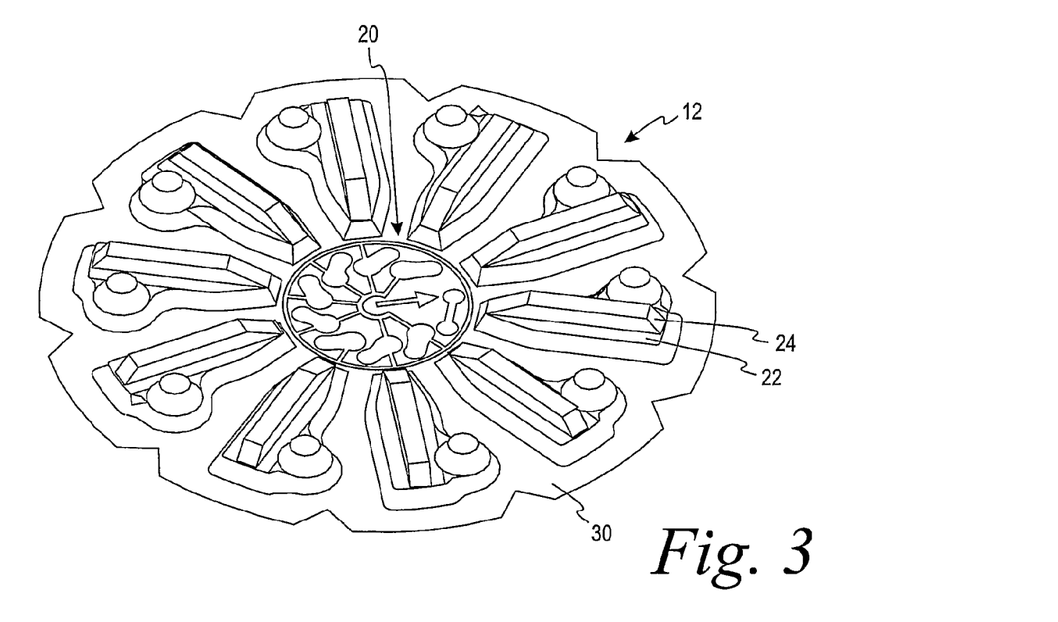
FIG. 3 is a sensor package according to one embodiment for use with the sensing instrument of FIG. 2.

Referring now to FIGS. 1-3, an instrument or meter 10 is illustrated. In FIG. 2, the inside of the instrument 10 is shown in the absence of a sensor package. One example of a sensor package (sensor package 12) is separately illustrated in FIG. 3. Referring back to FIG. 2, a base member 14 of the instrument 10 supports an auto-calibration plate 16 and a predetermined number of auto-calibration pins 18. As shown in FIG. 2, for example, the instrument 10 includes ten auto-calibration pins 18. It is contemplated that the number of auto-calibration pins may vary in number and shape from that shown in FIG. 2. The auto-calibration pins 18 are connected for engagement with the sensor package 12.

The sensor package 12 of FIG. 3 includes an interim auto-calibration circuit or label 20 and a plurality of test sensors 22. The plurality of test sensors 22 is used to determine concentrations of analytes. Analytes that may be measured include glucose, lipid profiles (e.g., cholesterol, triglycerides, LDL and HDL), microalbumin, hemoglobin $A_{1C}$, frictose, lactate, or bilirubin. It is contemplated that other analyte concentrations may be determined. The analytes may be in, for example, a whole blood sample, a blood serum sample, a blood plasma sample, other body fluids like ISF (interstitial fluid) and urine, and non-body fluids. As used within this application, the term "concentration" refers to an analyte concentration, activity (e.g., enzymes and electrolytes), titers (e.g., antibodies), or any other measure concentration used to measure the desired analyte.

In one embodiment, the plurality of test sensors 22 includes an appropriately selected enzyme to react with the desired analyte or analytes to be tested. An enzyme that may be used to react with glucose is glucose oxidase. It is contemplated that other enzymes may be used such as glucose dehydrogenase. An example of a test sensor is disclosed in U.S. Pat. No. 6,531,040 assigned to Bayer Corporation. It is contemplated that other test sensors may be used.

Calibration information or codes assigned for use in the clinical value computations to compensate for manufacturing variations between sensor lots are encoded on the auto-calibration circuit or label 20. The auto-calibration circuit or label 20 is used to automate the process of transferring calibration information (e.g., the lot specific reagent calibration information for the plurality of test sensors 22) such that the sensors 22 may be used with different instruments or meters. The auto-calibration pins 18 electrically couple with the auto-calibration circuit or label 20 when a cover 38 of the instrument 10 is closed and the circuit or label 20 is present. The auto-calibration circuit or label 20 will be discussed in detail in connection with FIG. 4.

According to one method, an analyte concentration of a fluid sample is determined using electrical current readings and at least one equation. In this method, equation constants are identified using the calibration information or codes from the auto-calibration circuit or label 20. These constants may be identified by (a) using an algorithm to calculate the equation constants or (b) retrieving the equation constants from a lookup table for a particular predefined calibration code that is read from the auto-calibration circuit or label 20. The auto-calibration circuit or label 20 may be implemented by digital or analog techniques. In a digital implementation, the instrument assists in determining whether there is conductance along selected locations to determine the calibration information. In an analog implementation, the instrument assists in measuring the resistance along selected locations to determine the calibration information.

Referring back to FIG. 3, the plurality of test sensors 22 is arranged around the auto-calibration circuit or label 20 and extends radially from the area containing the circuit or label 20. The plurality of sensors 22 of FIG. 3 is stored in individual cavities or blisters 24 and read by associated sensor electronic circuitry before one of the plurality of test sensors 22 is used. The plurality of sensor cavities or blisters 24 extends toward a peripheral edge of the sensor package 12. In this embodiment, each sensor cavity 24 accommodates one of the plurality of test sensors 22.

The sensor package 12 of FIG. 3 is generally circular in shape with the sensor cavities 24 extending from near the outer peripheral edge toward and spaced apart from the center of the sensor package 12. It is contemplated, however, that the sensor package may be of different shapes then depicted in FIG. 3. For example, the sensor package may be a square, rectangle, other polygonal shapes, or non-polygonal shapes including oval.

Figure 4:
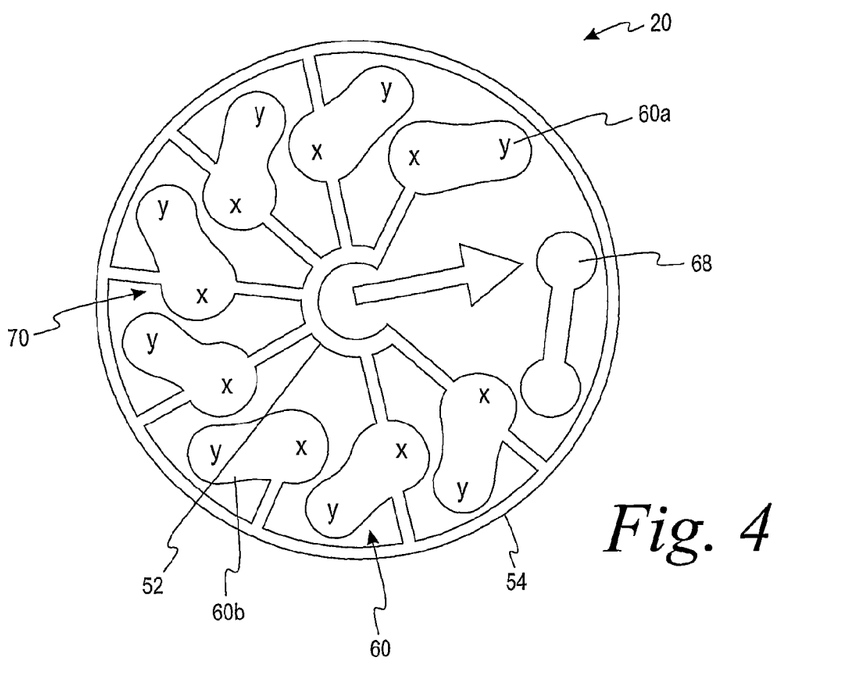
FIG. 4 is an interim auto-calibration circuit or label according to one embodiment of the invention.

The interim auto-calibration circuit or label 20 of FIG. 4 includes a first common connection (e.g., inner ring 52), and a second common connections (e.g., an outer ring 54). For some applications, the inner ring 52 represents logical 0s and the outer ring 54 represents logical 1s. It is contemplated that the inner ring or the outer ring may not be continuous. For example, the inner ring 52 is not continuous because it does not extend to form a complete circle. The outer ring 54, on the other hand, is continuous. The inner ring and the outer ring may both be continuous and in another embodiment the inner ring and the outer ring are not continuous. It is contemplated that the inner ring and outer rings may be shapes other than circular. Thus, the term "ring" as used herein includes non-continuous structures and shapes other than circular.

The auto-calibration circuit or label 20 includes a plurality of contact areas 60 (e.g., contact pads). The plurality of contact areas 60 is radially positioned around the circumference of the auto-calibration label 20. Each of the plurality of contact areas includes a first contact section (designated generally as a "x") and a second contact section (designated generally as a "y") being shorted together. The positioning of the plurality of contacts areas 60 permits the auto-calibration circuit or label 20 to be read by instruments or meters that are capable of contacting the plurality of contact areas 60. It is contemplated that the plurality of contact areas may be located in different positions than depicted in FIG. 4.

The interim auto-calibration circuit or label 20 has a plurality of electrical connections 70 being adapted to be utilized by the first instrument (e.g., an existing instrument) to auto-calibrate. The plurality of electrical connections 70 is also adapted to be utilized by the second instrument (e.g., an anticipated or future instrument) to auto-calibrate. The information from the plurality of electrical connections corresponds to the plurality of test sensors 22.

According to one embodiment, substantially all of the plurality of contact areas 60 are initially electrically connected to the first common connection (e.g., inner ring 52) and the second common connection (e.g., outer ring 54). To program the auto-calibration circuit or label, substantially all of the contact areas 60 in this embodiment will only be connected to one of the inner or outer rings 52, 54.

Figure 5:
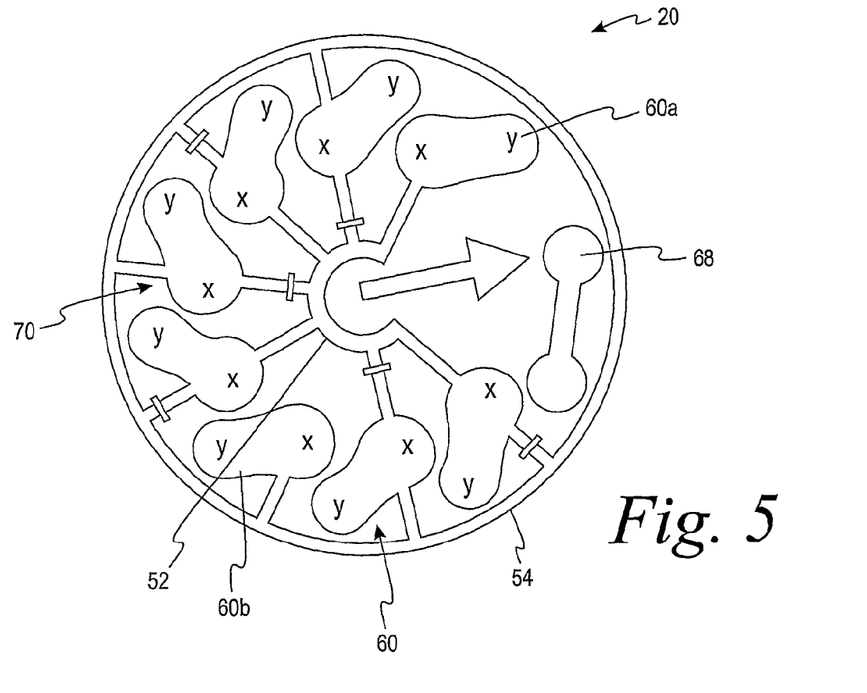
FIG. 5 is an interim auto-calibration circuit or label of FIG. 4 with cuts according to one pattern.

FIG. 4 does not depict a specific pattern, but rather shows a number of the potential connections of the plurality of contact areas to the first and second common connections. One example of a pattern of the auto-calibration circuit or label 20 is shown in FIG. 5 with cuts 94. It is contemplated that other patterns of the auto-calibration circuit or label may be formed.

Typically, at least one of the contact areas 60 will always be electrically connected to the first common connection (e.g., inner ring 52) and the second common connection (e.g., outer ring 54). For example, as shown in FIGS. 4 and 5, contact area 60a is always electrically connected to the inner ring 52. Additionally, contact area 60b is always electrically connected to the outer ring 54. By having individual contact areas 60 only connected to the inner or outer ring 52, 54 assists in maintaining a reliable instrument since any "no connect" may be sensed by the instrument software. Thus, a defective auto-calibration circuit or label or bad connection from the instrument may be automatically sensed by the instrument software.

The instrument may include several responses to reading the auto-calibration circuit or label. For example, responses may include the following codes: (1) correct read, (2) misread, (3) non-read, defective code, (4) non-read, missing label, and (5) read code out-of-bounds. A correct read indicates that the instrument or meter correctly read the calibration information. A misread indicates that the instrument did not correctly read the calibration information encoded in the circuit or label. In a misread, the circuit or label passed the integrity checks. A non-read, defective code indicates that the instrument senses that a circuit or label is present (continuity between two or more auto-calibration pins), but the circuit or label code fails one or more encoding rules (label integrity checks). A non-read, missing circuit or label indicates that the instrument does not sense the presence of a label (no continuity between any of the auto-calibration pins). A read code out-of-bounds indicates that the instrument senses an auto-calibration code, but the calibration information is not valid for that instrument.

The interim auto-calibration circuit or label 20 as discussed above is adapted to be assist in providing information to the first instrument and the second instrument. For example, the first instrument may be an existing instrument that is adapted to use a first reagent in which the glucose concentration is determined in a longer time period (e.g., 30 seconds). The second instrument may be a future instrument that is adapted to use a second reagent in which the glucose concentration is determined in a shorter time period (e.g., 10 seconds). The first reagent is not adapted to be used by the second instrument in determining the glucose concentration in the shorter time period.

The second instrument recognizes the interim auto-calibration circuit or label 20 in FIGS. 4 and 5 from the two adjacent pins 68 that are shorted together. Thus, the second instrument recognizes the circuit or label 20 as having a first reagent and determines the glucose concentration in the longer time period. It is contemplated that the second instrument may recognize the use of an interim auto-calibration circuit or label by other methods. For example, an interim auto-calibration circuit or label may be recognized by having two adjacent pins being isolated.

The auto-calibration label (e.g., auto-calibration circuits or labels 20) to be used with a first instrument and a second instrument may be formed according to the following method. A structure includes an electrically conductive layer is provided. A pattern is created on the electrically conductive layer using a laser to form an auto-calibration circuit or label. The pattern is adapted to be utilized by the first and second instrument to auto-calibrate. For example, the auto-calibration circuit or label may be used with one instrument to auto-calibrate. More typically, the auto-calibration circuit or label is used with at least two instruments to auto-calibrate in which the first and second instruments are different.

The electrically conductive layer may include conductive metals. Non-limiting examples of conductive metals that may be used include aluminum, copper, nickel, palladium, silver, platinum, gold, or combinations thereof. It is contemplated that other conductive metals may be used in forming the electrically conductive layer. The thickness of the electrically conductive layer may vary but generally is from about 10 to about 10,000 Angstroms. More typically, the electrically conductive layer is from about 100 to about 2,500 Angstroms. In one embodiment, the structure consists of the electrically conductive layer such as, for example, a single layer of aluminum or nickel.

In another embodiment, the structure includes a polymeric portion (e.g., polymeric film) and a metallic portion. For example, the structure may be a metalized polymeric film, a coextruded metalized polymeric film, or a laminated metalized polymeric film. It is contemplated that other structures may be employed in the methods of the present invention. The polymeric portion to be used in these structures may be formed from a variety of polymeric materials or filled-polymeric materials. For example, the polymeric portion may be made from materials such as polyethylene, polypropylene, oriented polypropylene (OPP), cast polypropylene (CPP), polyethylene terephthlate (PET), polyether ether ketone (PEEK), polyether sulphone (PES), polycarbonate, or combinations thereof. The thickness of the polymeric film is generally from about 6 to about 250 microns. More specifically, the thickness of the polymeric film is generally from about 25 to about 250 microns.

The auto-calibration circuits or labels (e.g., auto-calibration circuits or labels 20) of the present invention may be formed and then attached to a sensor package (e.g., sensor package 12). The auto-calibration circuit or label may be attached to the sensor package via, for example, an adhesive or other attachment method. In another method, at least a portion of the surface of the sensor-package base includes an electrically conductive layer. The pattern is created on this electrically conductive layer using a laser. Thus, in this method the electrically conductive metal is part of the product packaging.

A laser creates the pattern on the electrically conductive layer to form an auto-calibration circuit or label. The laser functions by cutting the electrically conductive layer in selected locations to form the desired auto-calibration circuit or label. There are many different types of laser that may be used in creating the pattern on the electrically conductive layer. The lasers to be used in the present invention remove the electrically conductive layer to isolate regions electrically.

One laser that may be used in the present invention is a solid-state laser such as a yttrium-based laser. Examples of yttrium-based lasers that are commercially available are Rofin DY-HP Series, Telesis ECLIPSE® TLM, or Telesis ZENITH® Series. It is contemplated that other yttrium-based lasers may be used.

Another type of laser that may be used in the present invention is a gas laser such as a carbon dioxide-based laser. Examples of carbon dioxide-based lasers that are commercially available are Rofin FA Series, Telesis SABRE® Series, or Keyence ML-G Series $CO_2$. It is contemplated that other carbon dioxide-based lasers may be used.

A further type of laser that may be used is an Excimer laser. Excimer lasers use reactive gases, such as chlorine and fluorine, that are mixed with inert gases such as argon, krypton or xenon. To obtain optimum ablation, the wavelength may need to be matched to the selected metal. An example of an Excimer laser that is commercially available is Lambda Physik $F_2$ Series. It is contemplated that other Excimer lasers may be used. It is also contemplated that other lasers may be used in forming the auto-calibration circuits or labels of the present invention other than those discussed above in the specific examples above.

According to one method, the pattern may be created using a mask and a laser such as, for example, an Excimer laser or a carbon dioxide-based laser. Examples of patterns using a mask are shown in FIGS. 4 and 5. It is contemplated that various masks may work in conjunction with the laser in forming the auto-calibration circuit or label. One example of a mask is a chrome-on-glass mask in which the beam of light is only allowed to pass through selected areas to form the auto-calibration circuit or label.

Figure 6:
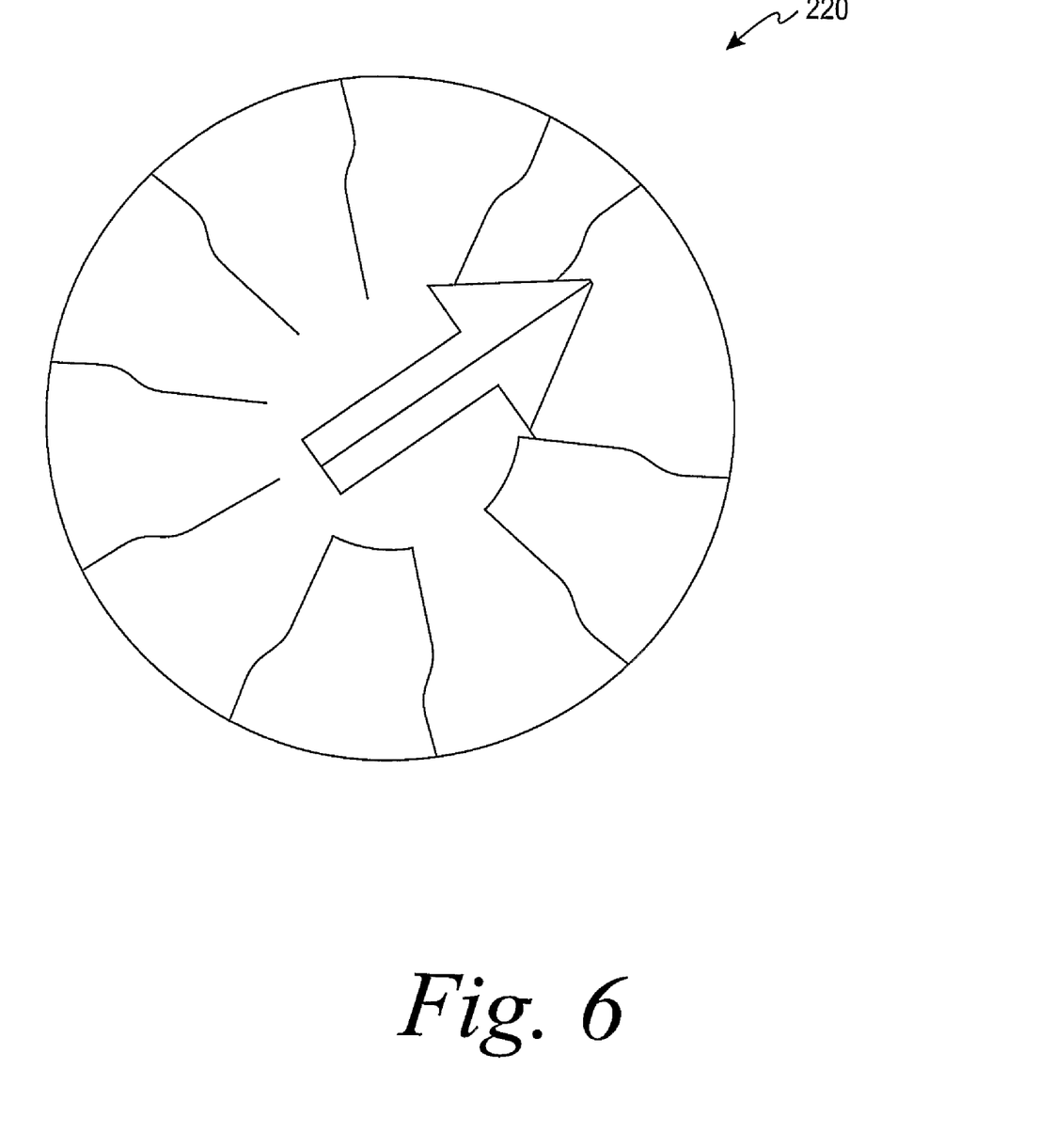
FIG. 6 is an interim auto-calibration circuit or label according to another embodiment.

According to one method, the pattern may be created using direct writing of the lines. In this method, the laser beam of light is moved so as to form the desired pattern. An example of an auto-calibration circuit or label formed using this method is shown in FIG. 6 with auto-calibration circuit or label 220. It is contemplated that other patterns may be created using direct writing of the lines. Lasers that produce a beam of energy capable of removing the metal layer and that can be moved to form a pattern may be used in this method. Non-limiting examples of such lasers are carbon dioxide-based lasers and yttrium-based lasers such as yttrium aluminum garnet (YAG) lasers.

The methods of the present invention are desirable because they are adapted to work in tighter spaces. For example, the methods of the present invention can produce spaces between adjacent electrical areas of from about 1 to about 10 mils, which allows for the possibility of tighter tolerances and/or a smaller auto-calibration area.

The auto-calibration circuit or label 20 of FIGS. 4 and 5 is generally circular shaped. It is contemplated, however, that the auto-calibration circuit or label may be of different shapes than depicted in FIGS. 4 and 5. For example, the auto-calibration circuit or label may be a square, rectangle, other polygonal shapes, and non-polygonal shapes including oval. It is also contemplated that the contacts areas may be in different locations than depicted in FIGS. 4 and 5. For example, the contacts may be in a linear array.

It is contemplated that the auto-calibration circuit or label 20 may be used with a first instrument other than the first instrument 10 depicted in FIGS. 1 and 2. The auto-calibration circuit or label 20 may also be used in other type of sensor packs than sensor package 12. For example, the auto-calibration circuits or labels may be used in sensor packages such as a cartridge with a stacked plurality of test sensors or a drum-type sensor package.

Alternative Embodiment A

An interim auto-calibration circuit or label adapted to be used with a sensor package, the sensor package being adapted to be used with a first instrument and a second instrument, the first instrument being adapted to determine an analyte concentration in a fluid sample, the second instrument being adapted to determine the analyte concentration in the fluid sample, the first instrument being different from the second instrument, the first instrument including a first plurality of pins in a first pattern, the second instrument including a second plurality of pins in a second pattern, the first and second patterns being different, the sensor package comprising:

a plurality of electrical connections that includes a plurality of contact areas, each of the plurality of contact areas having a first contact section and a second contact section being shorted together, each of the first contact sections being adapted to contact a respective one of the first plurality of pins, each of the second contact sections being adapted to contact a respective one of the second plurality of pins, the plurality of electrical connections assisting in conveying information corresponding to the plurality of test sensors, the information being adapted to be utilized by the first instrument and the second instrument to auto-calibrate for the plurality of test sensors.

Alternative Embodiment B

The interim label of Alternative Embodiment A wherein the interim auto-calibration circuit or label further includes a first common connection and a second common connection.

Alternative Embodiment C

The interim label of Alternative Embodiment B wherein the first common connection is an inner ring and the second common connection is an outer ring.

Alternative Embodiment D

The interim label of Alternative Embodiment C wherein at least one of the inner ring and the outer ring is continuous.

Alternative Embodiment E

The interim label of Alternative Embodiment D wherein the outer ring is continuous.

Alternative Embodiment F

The interim label of Alternative Embodiment A wherein the auto-calibration circuit or label is generally circular shaped.

Alternative Embodiment G

A sensor package adapted to be used in a first instrument and a second instrument, the first instrument being adapted to determine an analyte concentration in a fluid sample, the second instrument being adapted to determine the analyte concentration in the fluid sample, the first instrument being different from the second instrument, the first instrument including a first plurality of pins in a first pattern, the second instrument including a second plurality of pins in a second pattern, the first and second patterns being different, the sensor package comprising:

a plurality of test sensors being adapted to receive the fluid sample and operable with the first instrument and the second instrument; and an interim auto-calibration circuit or label being adapted to be used with the first instrument and the second instrument, the auto-calibration circuit or label including a plurality of electrical connections, the plurality of electrical connections including a plurality of contact areas, each of the plurality of contact areas having a first contact section and a second contact section being shorted together, each of the first contact sections being adapted to contact a respective one of the first plurality of pins, each of the second contact sections being adapted to contact a respective one of the second plurality of pins, the plurality of electrical connections assisting in conveying information corresponding to the plurality of test sensors, the information being adapted to be utilized by the first instrument and the second instrument to auto-calibrate for the plurality of test sensors.

Alternative Embodiment H

The sensor package of Alternative Embodiment G wherein the interim auto-calibration circuit or label further includes a first common connection and a second common connection.

Alternative Embodiment I

The sensor package of Alternative Embodiment H wherein the first common connection is an inner ring and the second common connection is an outer ring.

Alternative Embodiment J

The sensor package of Alternative Embodiment I wherein at least one of the inner ring and the outer ring is continuous.

Alternative Embodiment K

The sensor package of Alternative Embodiment J wherein the outer ring is continuous.

Alternative Embodiment L

The sensor package of Alternative Embodiment G wherein the auto-calibration circuit or label is generally circular shaped.

Alternative Embodiment M

The sensor package of Alternative Embodiment G further including a plurality of cavities containing a respective one of the plurality of test sensors, the plurality of cavities being arranged around the auto-calibration circuit or label.

Alternative Embodiment N

The sensor package of Alternative Embodiment G wherein the analyte is glucose.

Alternative Embodiment O

A system for determining an analyte concentration in a fluid sample, the system comprising:

a test sensor adapted to receive the fluid sample;

a processor responsive to the test sensor and adapted to perform a predefined test sequence for measuring a predefined parameter value; and an interim auto-calibration circuit or label being adapted to be used with the first instrument and the second instrument, the auto-calibration circuit or label including a plurality of electrical connections, the plurality of electrical connections including a plurality of contact areas, each of the plurality of contact areas having a first contact section and a second contact section being shorted together, each of the first contact sections being adapted to contact a respective one of the first plurality of pins, each of the second contact sections being adapted to contact a respective one of the second plurality of pins, the plurality of electrical connections assisting in conveying information corresponding to the plurality of test sensors, the information being adapted to be utilized by the first instrument and the second instrument to auto-calibrate for the plurality of test sensors.

Alternative Embodiment P

The system of Alternative Embodiment O wherein the analyte is glucose.

While the present invention has been described with reference to one or more particular embodiments, those skilled in the art will recognize that many changes may be made thereto without departing from the spirit and scope of the present invention. Each of these embodiments, and obvious variations thereof, is contemplated as falling within the spirit and scope of the invention as defined by the appended claims.

The invention claimed is:

1. An interim auto-calibration circuit or label adapted to be used with a sensor package, the sensor package being adapted to be used with a first instrument and a second instrument, the first instrument being adapted to determine an analyte concentration in a fluid sample, the second instrument being adapted to determine the analyte concentration in the fluid sample, the first instrument being different from the second instrument, the first instrument including a first plurality of pins in a first pattern, the second instrument including a second plurality of pins in a second pattern, the first and second patterns being different, the sensor package comprising:

a plurality of electrical connections that includes a plurality of contact areas, each of the plurality of contact areas having a first contact section and a second contact section being shorted together, each of the first contact sections being adapted to contact a respective one of the first plurality of pins, each of the second contact sections being adapted to contact a respective one of the second plurality of pins, the first contact section and the second contact section is located in a single layer, the plurality of electrical connections assisting in conveying information corresponding to the plurality of test sensors, the information being adapted to be utilized by the first instrument and the second instrument to auto-calibrate for the plurality of test sensors.

2. The interim label of claim 1, wherein the interim auto-calibration circuit or label further includes a first common connection and a second common connection.

3. The interim label of claim 2, wherein the first common connection is an inner ring and the second common connection is an outer ring.

4. The interim label of claim 3, wherein at least one of the inner ring and the outer ring is continuous.

5. The interim label of claim 4, wherein the outer ring is continuous.

6. The interim label of claim 1, wherein the auto-calibration circuit or label is generally circular shaped.

7. A sensor package adapted to be used in a first instrument and a second instrument, the first instrument being adapted to determine an analyte concentration in a fluid sample, the second instrument being adapted to determine the analyte concentration in the fluid sample, the first instrument being different from the second instrument, the first instrument including a first plurality of pins in a first pattern, the second instrument including a second plurality of pins in a second pattern, the first and second patterns being different, the sensor package comprising:
  a plurality of test sensors being adapted to receive the fluid sample and operable with the first instrument and the second instrument; and
  an interim auto-calibration circuit or label being adapted to be used with the first instrument and the second instrument, the auto-calibration circuit or label including a plurality of electrical connections, the plurality of electrical connections including a plurality of contact areas, each of the plurality of contact areas having a first contact section and a second contact section being shorted together, each of the first contact sections being adapted to contact a respective one of the first plurality of pins, each of the second contact sections being adapted to contact a respective one of the second plurality of pins, the first contact section and the second contact section is located in a single layer, the plurality of electrical connections assisting in conveying information corresponding to the plurality of test sensors, the information being adapted to be utilized by the first instrument and the second instrument to auto-calibrate for the plurality of test sensors.

8. The sensor package of claim 7, wherein the interim auto-calibration circuit or label further includes a first common connection and a second common connection.

9. The sensor package of claim 8, wherein the first common connection is an inner ring and the second common connection is an outer ring.

10. The sensor package of claim 9, wherein at least one of the inner ring and the outer ring is continuous.

11. The sensor package of claim 10, wherein the outer ring is continuous.

12. The sensor package of claim 7, wherein the auto-calibration circuit or label is generally circular shaped.

13. The sensor package of claim 7, further including a plurality of cavities containing a respective one of the plurality of test sensors, the plurality of cavities being arranged around the auto-calibration circuit or label.

14. The sensor package of claim 7, wherein the analyte is glucose.

15. A system for determining an analyte concentration in a fluid sample, the system comprising:
  a test sensor adapted to receive the fluid sample;
  a processor responsive to the test sensor and adapted to perform a predefined test sequence for measuring a predefined parameter value; and
  an interim auto-calibration circuit or label being adapted to be used with the first instrument and the second instrument, the auto-calibration circuit or label including a plurality of electrical connections, the plurality of electrical connections including a plurality of contact areas, each of the plurality of contact areas having a first contact section and a second contact section being shorted together, each of the first contact sections being adapted to contact a respective one of the first plurality of pins, each of the second contact sections being adapted to contact a respective one of the second plurality of pins, the first contact section and the second contact section is located in a single layer, the plurality of electrical connections assisting in conveying information corresponding to the plurality of test sensors, the information being adapted to be utilized by the first instrument and the second instrument to auto-calibrate for the plurality of test sensors.

16. The system of claim 15, wherein the analyte is glucose.

* * * * *